United States Patent
Sylwester

(10) Patent No.: US 7,157,004 B1
(45) Date of Patent: Jan. 2, 2007

(54) FREEZE DRYING FOR GAS CHROMATOGRAPHY STATIONARY PHASE DEPOSITION

(75) Inventor: Alan P. Sylwester, Livermore, CA (US)

(73) Assignee: Sandia Corporation, Albuquerque, NM (US)

( * ) Notice: Subject to any disclaimer, the term of this patent is extended or adjusted under 35 U.S.C. 154(b) by 282 days.

(21) Appl. No.: 10/998,847

(22) Filed: Nov. 29, 2004

(51) Int. Cl.
B01D 15/08 (2006.01)

(52) U.S. Cl. .................. 210/656; 210/198.2; 95/88; 96/101

(58) Field of Classification Search .............. 210/635, 210/656, 659, 198.2, 502.1; 141/12, 80; 95/88; 96/101
See application file for complete search history.

(56) References Cited

U.S. PATENT DOCUMENTS

| | | | | |
|---|---|---|---|---|
| 3,957,651 A | * | 5/1976 | Kesting | 210/490 |
| 4,131,542 A | * | 12/1978 | Bergna et al. | 210/656 |
| 4,832,881 A | * | 5/1989 | Arnold et al. | 264/29.7 |
| 5,028,335 A | * | 7/1991 | Sleytr et al. | 210/638 |
| 5,770,087 A | * | 6/1998 | Reuter | 210/657 |
| 5,780,593 A | * | 7/1998 | Lihme et al. | 530/361 |
| 5,814,225 A | * | 9/1998 | Shanbrom | 210/656 |
| 6,096,216 A | * | 8/2000 | Shanbrom et al. | 210/638 |
| 6,663,697 B1 | * | 12/2003 | Kottenstette et al. | 96/101 |
| 6,709,743 B1 | * | 3/2004 | Draveling | 428/402 |
| 2004/0211730 A1 | * | 10/2004 | Zhang et al. | 210/656 |

* cited by examiner

Primary Examiner—Ernest G. Therkorn
(74) Attorney, Agent, or Firm—Min, Hsieh, & Hack LLP

(57) ABSTRACT

The present disclosure relates to methods for deposition of gas chromatography (GC) stationary phases into chromatography columns, for example gas chromatography columns. A chromatographic medium is dissolved or suspended in a solvent to form a composition. The composition may be inserted into a chromatographic column. Alternatively, portions of the chromatographic column may be exposed or filled with the composition. The composition is permitted to solidify, and at least a portion of the solvent is removed by vacuum sublimation.

20 Claims, 1 Drawing Sheet

FREEZE DRYING FOR GAS CHROMATOGRAPHY STATIONARY PHASE DEPOSITION

This invention was developed under Contract DE-AC04-94AL85000 between Sandia Corporation and the U.S. Department of Energy. The U.S. Government has certain rights in this invention.

FIELD

The present disclosure relates to fabrication processes for columns used in chromatography, for example gas chromatography (GC). In particular, the disclosure relates to deposition of stationary phases into GC columns.

INTRODUCTION

Analyses of chemical samples have long been carried out using chromatographic methods. Generally, chromatography involves separation of chemical species transported in a mobile phase (typically as a liquid, gas, or supercritical fluid) in which the chemical species, commonly referred to as analytes, are dissolved or otherwise carried along by the mobile phase. The mobile phase is forced through or past a stationary phase which is typically porous and immiscible in the mobile phase.

The chemical species of interest will have different affinities for the stationary phase, as well as different solubilities in the mobile phase. As the mobile phase is forced through and/or past the stationary phase, the analytes are carried through the stationary phase at different velocities, the net result being separation of the chemical species in the sample.

In a common approach to high-pressure liquid chromatography, narrow tubes called columns are packed with a particulate stationary phase, through which the mobile phase is forced. A sample of the chemical species to be separated is typically injected together with a small amount of the mobile phase, and the sample is then transported through the column by continuous addition of pure mobile phase.

Many types of stationary phases are used in chromatographic analysis. These can have a variety of physicochemical properties, and can also have differing physical aspects. In the simplest form, the stationary phase is simply a solid, for example solid particles, and the analyte is adsorbed on the surface of the solid.

Chromatographic columns are usually based upon open tubular columns or tubular packed beds. Open tubular columns are typically about 0.5 millimeters in inside diameter and 5 to 30 meters in length, with a submicron polymer layer on the inside of the tube making up the stationary phase. Tubular packed beds are typically about 3 millimeters in inside diameter and 2–3 meters in length, and are filled with a solid powder whose surface or surface coating forms the stationary phase.

Chromatographic columns must have considerable length to provide adequate separation of analytes. However, there is a high cost to be paid for needing such long columns. The column is typically maintained at a constant and elevated temperature, which requires a large insulated cabinet and hundreds of watts for operation. Long columns are often fragile, and this may limit the potential for making conventional chromatographic columns with significantly reduced size and thermal requirements.

There are a number of potential applications for chromatographic analysis that benefit from incorporation of smaller and thermally efficient chromatographic columns. These may include, for example, applications related to process control, industrial hygiene, environmental analysis, detection of chemical and biological warfare agents, and many more.

Miniature chromatographic columns may be built using microfabrication techniques based on silicon lithography, similar to those used to fabricate LIGA (an acrronym for the German words for lithography, electroplating, and molding) and microelectromechanical systems (MEMS). For example, U.S. Pat. No. 6,663,697 (the disclosure of which is incorporated by reference herein in its entirety), describes a microfabricated chromatographic column containing particulate chromatographic media. The column comprises a high aspect ratio channel in the form of a spiral groove etched into the surface of a silicon substrate. When formed, the groove is open at the surface of the silicon substrate, and is later sealed by attaching a cover plate, thereby converting the spiral groove into a spiral column with an input end and an output end. A mobile phase and the sample materials are introduced into the input end of the spiral column, travel through the column, and exit the column at the output end.

A particulate chromatographic medium resides within the spiral column. A packing retainer is fabricated near the output end of the spiral column. The function of the packing retainer is to prevent the particles of the chromatographic medium from being swept out of the spiral column by the flow of the mobile phase, while at the same time avoiding an undue flow resistance to the mobile phase.

Many commercial particulate chromatographic media have particles with sizes ranging from 50 to 100 microns, and have submicrogram weights. Efficient and effective packing of such media in a column having a cross section only a few times larger in size is a difficult problem, and one in which the solution is a vital part of utilizing such miniaturized chromatographic columns.

There are two general approaches to filling these miniature chromatographic columns. In the first, the chromatographic column is assembled. For example, the cover plate will be sealed to the substrate of the chromatographic column, and then a particulate chromatographic medium is inserted through the input to the column or through a separate medium filling aperture.

In the second approach, the chromatographic column is filled prior to assembly. Here, the elongated groove on the substrate of the miniaturized chromatographic column is filled with a particulate chromatographic medium before the cover plate is sealed to the sealing plane of the substrate, thereby forming the desired packed chromatographic column.

To use miniaturized chromatographic columns, a particulate chromatographic medium must be introduced within the elongated column. This column can be as little as 2–3 times larger in cross-sectional dimensions, as are the particles of the chromatographic medium, and the length to width ratio of the column can easily exceed 1000.

The small dimensions involved may present a number of problems that are not serious in conventional chromatographic columns. It takes very little obstructive force to prevent the very small particles from entering and becoming densely packed in the column. In particular, the effect of electrostatic forces are enhanced by the small separations between the size of the particles and the size of the column, and the large dielectric constant of the materials generally used to fabricate such columns.

Therefore, it would be desirable to provide processes that can efficiently install or pack a stationary phase into a chromatography column, such as a miniature gas chromatography column. The present disclosure provides an improved process for gas chromatography column stationary phase deposition.

SUMMARY

According to one aspect of the present disclosure, there is provided a process for introducing a chromatographic medium into a chromatography column, comprising contacting a column with a composition comprising a solvent and a chromatography medium, wherein said composition is in the liquid phase; allowing the composition to solidify; and removing at least a portion of the solvent by vacuum sublimation.

According to another aspect of the present disclosure, there is provided a process for filling an elongated groove with a chromatographic medium, wherein the elongated groove comprises part of an unassembled miniaturized chromatographic column, said process comprising exposing said elongated groove to a composition comprising a solvent and a chromatographic medium; and removing at least a portion of the solvent from the elongated groove by vacuum sublimation.

According to yet another aspect of the present disclosure, there is provided a process for deposition of a stationary phase in a microfabricated gas chromatography column, comprising combining the stationary phase with a solvent to form a composition, wherein the solvent is suitable for removal by vacuum distillation; filling at least a portion of the microfabricated gas chromatography column with the composition; and removing at least a portion of the solvent in the composition by vacuum sublimation.

It is to be understood that both the foregoing general description and the following description of various embodiments are exemplary and explanatory only and are not restrictive.

BRIEF DESCRIPTION OF THE DRAWING

The accompanying drawing, which is incorporated in and constitutes a part of this specification, illustrates various embodiments.

DESCRIPTION OF VARIOUS EMBODIMENTS

Figure 1:
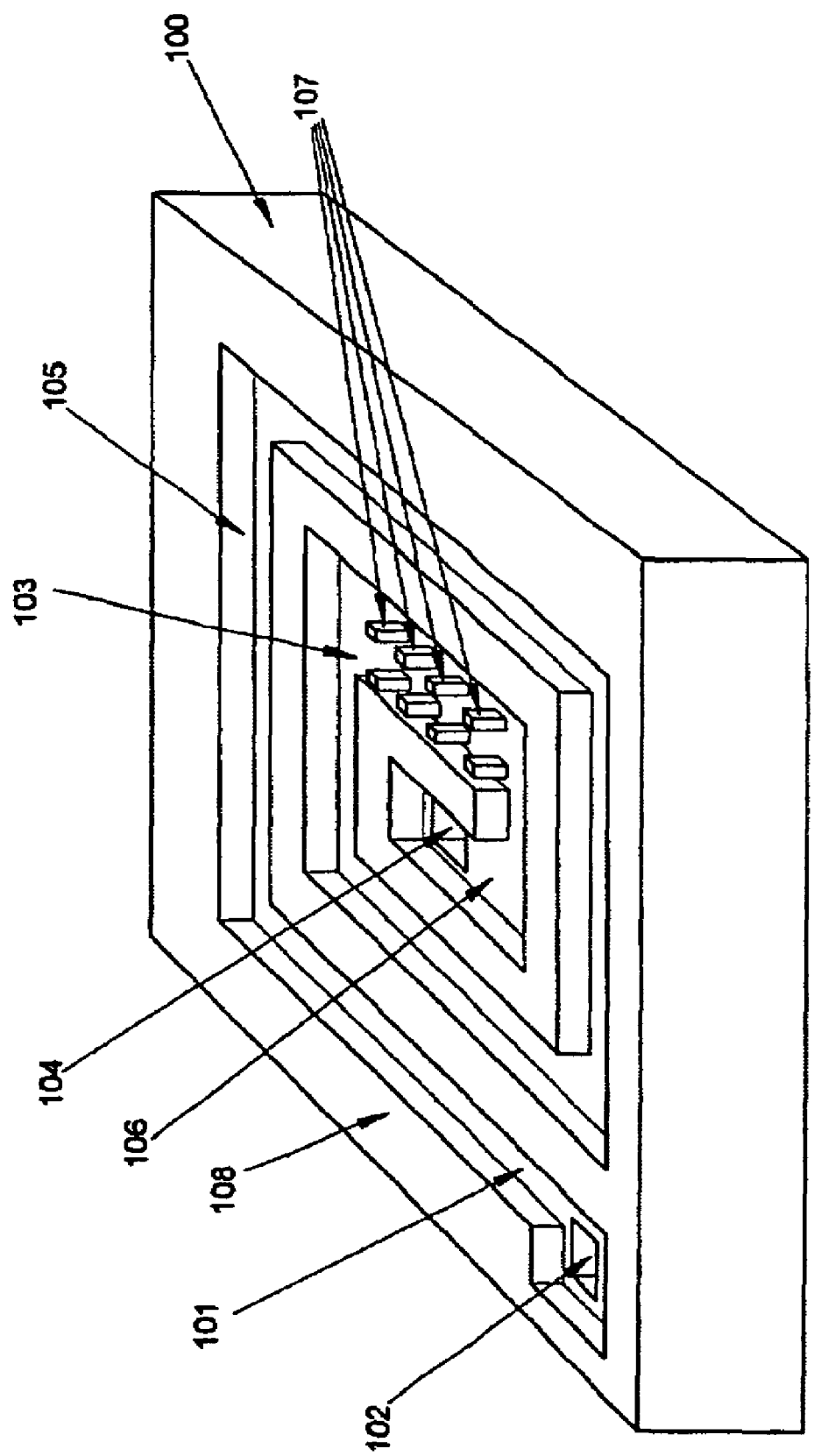
FIG. 1 illustrates a substrate containing a microfabricated GC column.

Microfabricated systems using gas chromatographic separations have typically employed a packed or coated GC column. Reproducible deposition of the GC column stationary phase—typically a bead packing, a film coating or an expanded polymeric structure—represents a significant challenge for high-volume, wafer-scale production. A fundamental challenge attendant with microfabricated systems is deposition of stationary phases in very small dimensions (e.g., small widths for high aspect ratio columns, or small diameters for circular columns). For example, GC columns may have a length ranging from 1 cm to 3 m, for example 10 cm to 2 m. The columns may have a footprint ranging from 0.1 $cm^2$ to 5 $cm^2$, for example 0.5 $cm^2$ to 2 $cm^2$. Such microfabricated systems provide the advantages of better separation per unit length of column, and faster separations, but significant challenges in fabrication and volume production. These small dimensions may benefit from improved control of stationary phase deposition to improve uniformity and yield of reproducible devices.

The present disclosure relates to processes for packing microfabricated GC columns using solutions of polymeric stationary phases, or slurries of the stationary phase, in solvents that lend themselves to removal by vacuum sublimation, suitably after fabrication of the GC system is completed. Solution deposition and vacuum sublimation may be implemented at the wafer scale and lend themselves to improving the reproducibility and batch processing of GC-based chemical Microsystems.

This improvement for microfabricated GC systems employs compositions comprising stationary phases, for example polymeric stationary phases, in solvents that lend themselves to at least partial removal by vacuum sublimation. According to one aspect of the disclosure, the solvent is removed after fabrication of the GC system is completed. Solution deposition and vacuum sublimation may be implemented at the wafer scale, thereby improving the reproducibility and batch processing of CG-based chemical Microsystems.

Sublimation refers to a solid changing directly to a vapor state. More specifically, sublimation is a process in which a substance, such as ice, goes from a solid to a gas without going through a liquid phase. For some solvents, sublimation can occur at atmospheric pressure. However, for some aspects of the disclosure, it may be advantageous to increase the rate at which the molecules sublimate by decreasing the pressure above the surface of the substrate. This may be accomplished by subjecting the solvent to a vacuum or a suitably low pressure to aid its sublimation.

Suitable stationary phases include solid stationary phases. They may include high surface area materials that effect separation by the interaction of the surface with the sample analytes or compounds. In packed columns, materials such as silica gel, porous silica, synthetic zeolites, alumina, activated carbon, graphitized carbon, carbon molecular sieves and styrene divinylbenzene resins have been used. Inorganic materials, such as silica gel, porous silica, molecular sieves, and alumina have been used, and they may be activated by heating to drive off water and to make the surfaces chromatographically active, i.e. capable of effecting chromatographic separations. For the separation of lower molecular weight compounds, silica gel may also be used.

Solvent systems suitable for the purposes of the present disclosure include solvents that, for example, (1) exhibit appropriate solution strength (e.g., are capable of dissolving or suspending polymers and stationary phases as particles); (2) exhibit appropriate wetting properties in contact with surfaces such as, for example, silicon, silicon oxides and polymeric surfaces; (3) have appropriate phase transfer temperatures for processing; and (4) provide vapor pressures appropriate for removal by vacuum sublimation.

A number of solvents may have the appropriate properties for use in accordance with the present disclosure. Suitable non-limiting examples of solvents having appropriate solution and physical properties include, but are not limited to: maleic anhydride, dimethyl sulfone, cyclohexanol, paradichlorobenzene, norcamphor, dimethyl formamide, 1-methyl-2-pyrrolidone, and succinonitrile. The solvents may be used in combination and/or in aqueous solution, for example as 70–90% methyl sulfone with 10–30% cyclohexanol, 85–95% methyl sulfone with 5–15% water, and 40–60% methyl sulfone with 60–40% norcamphor (all solvent percentages are given as weight/weight, except for aqueous methyl sulfone, which is given as weight/volume).

A number of solvent systems may be used for the fabrication of uniform microporous polymer structures in bulk. These solvent systems may have some of the desired chemical and physical properties that are suitable for the purposes of the present disclosure. See, for example, U.S. Pat. No. 4,832,881 (the disclosure of which is incorporated by reference herein in its entirety).

In accordance with the present disclosure, the appropriate stationary phase is dissolved or suspended in the solvent. The dissolution or suspension of the stationary phase in the solvent may be conducted at a temperature ranging from 100° C. to 200° C. According to one aspect of the disclosure, the dissolution temperature ranges from 150° C. to 160° C.

The resulting composition is placed in contact with a GC column, a wafer of micro GC columns, or Microsystems containing GC columns. The column is contacted with the composition by any suitable method. Suitable non-limiting examples of contacting the column with the composition include spin-coating the composition onto a wafer comprising the column, suctioning the composition into the column, spray-coating the composition onto a wafer comprising the column, and submerging a wafer comprising the column into the composition. According to one aspect of the present disclosure, the column comprises an elongated groove, and the elongated groove is exposed to the composition by applying centrifugal forces to pack and retain the composition into the elongated groove. According to another aspect of the disclosure, the elongated groove contains an input aperture, and the groove is filled by inserting the composition through the input aperture. According to another aspect, the elongated groove contains an output aperture, and a vacuum is applied to the output aperture, such that the composition is suctioned from the input aperture. The compositions are permitted to wet the surfaces of the GC columns uniformly, or at least substantially uniformly. An excess of solvent and/or chromatographic media may be removed from the surface of the wafer.

Suitably, the composition is then permitted to cool to, e.g., room temperature, or any other temperature at which the composition solidifies. The composition may be permitted to cool at various rates. A suitable cooling rate may be, for example, 10° C. per minute. Near room temperature, these stationary phase solutions are frozen solid. After the composition solidifies, the solvent may be removed by vacuum sublimation. Following removal of solvent by vacuum sublimation, additional processing to seal the columns through adhesive bonding, diffusion bonding or anodic bonding of a cover layer (e.g., glass, polymer or silicon) may be accomplished. According to another aspect of the disclosure, following solidification of the composition, the column is sealed. Next, the residual solvent is removed by sublimation in, e.g., a vacuum oven.

In accordance with the present disclosure, dilute compositions may be used to deposit uniform expanded high surface area stationary phases as monoliths or coatings or dense arrays of particulate packings. According to one aspect of the disclosure, multiple columns are processed simultaneously at the wafer level to improve yield and reproducibility of devices in processes amenable to batch microfabrication.

An exemplary implementation is described below for the purposes of illustrating various features of the present disclosure. The choice of any implementations over another is not intended to limit the scope of the claimed invention. The GC column stationary phase deposition process is demonstrated with reference to a miniaturized chromatographic column, a schematic of which is shown in FIG. 1.

In FIG. 1 appears a substrate 100, whose top surface has been configured to define a sealing plane 108, an elongated groove 101, a sample input aperture 102, a packing retainer 103, and a sample output aperture 104. In this implementation, the elongated groove 101 takes a square spiral path, and has a nominally quadrilateral cross section. The sample input aperture 102 and the sample output aperture 104 in this implementation penetrate substrate 100, thereby enabling access to the elongated groove 101 from the back side of the substrate. Other possibilities will be clear to one skilled in the art.

A miniaturized chromatographic column may comprise a substrate 100 comprising crystalline or glassy semiconductors or insulators, as will the cover plate (not shown). The column may be prepared by conventional micromachining techniques. The easiest materials to be used in conventional micromachining techniques include silicon crystal, amorphous silicon, and silicon oxide-containing glasses. However, many other materials can be so utilized, and can be required depending on the ultimate application of the device.

The features defined by the configuration of the top surface of the substrate 100 may be fabricated therein by etching said surface, e.g., using Bosch and other etching processes appropriate for forming the desired surface configuration in the material of the substrate. Other suitable fabrication techniques comprise mechanical machining of the substrate, e.g., using electron discharge machining. The negative of these features could be fabricated in one material by one of the above techniques, and then the desired features could be replicated in a second material using techniques such as hot embossing or injection molding.

The packing retainer 103 divides the elongated groove 101 into a stationary medium portion 105 and an output portion 106. The packing retainer 103 comprises a series of blocking elements 107, which are so positioned within the elongated groove 101 as to block passage of a particulate chromatographic medium (not shown) from stationary medium portion 105 into output portion 106.

As an illustration, a composition is formed from (1) a particulate chromatographic medium comprising silica gel, and (2) a solvent system comprising 80% methylsulfone/20% cyclohexanol. The ingredients are combined and thoroughly mixed at a temperature of 150° C. The substrate 100 is completely submersed in the composition, and then removed. Excess composition is removed from every surface but for elongated groove 101 by pulling an elongated blade across planar surface 108.

The substrate 100 is then placed into a sealed chamber and maintained at approximately room temperature. As the substrate cools, the composition hardens. The chamber is then subjected to a pressure of approximately 0.5 ATM. The solvent sublimates from the composition, leaving the silica gel in place.

A cover plate (not shown) is then sealed atop substrate 100 so as to convert elongated groove 101 into an elongated column capable of confining a particulate chromatographic medium through which a mobile phase can be circulated. The sealing can be accomplished by a number of techniques, including welding, soldering, use of adhesives, anodic bonding, thermal fusion bonding, deformation sealing, and many others.

The above-exemplified process yields a microfabricated column containing a sufficient amount of chromatographic media. Since the solvent is in a solid form during removal, surface tension forces are not active and will not result in an excess of stationary phase or packing material in the corners of rectangular columns (this is a common problem that limits the effectiveness or rectangular columns to date).

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "less than 10" includes any and all subranges between (and including) the minimum value of zero and the maximum value of 10, that is, any and all subranges having a minimum value of equal to or greater than zero and a maximum value of equal to or less than 10, e.g., 1 to 5.

It is noted that, as used in this specification and the appended claims, the singular forms "a," "an," and "the," include plural referents unless expressly and unequivocally limited to one referent. Thus, for example, reference to "a charged species" includes two or more different charged species. As used herein, the term "include" and its grammatical variants are intended to be non-limiting, such that recitation of items in a list is not to the exclusion of other like items that can be substituted or added to the listed items.

It will be apparent to those skilled in the art that various modifications and variations can be made to various embodiments described herein without departing from the spirit or scope of the present teachings. Thus, it is intended that the various embodiments described herein cover other modifications and variations within the scope of the appended claims and their equivalents.

What is claimed is:

1. A process for introducing a chromatographic medium into a chromatography column, comprising:
    contacting a column with a composition comprising a solvent and a chromatography medium, wherein said composition is in the liquid phase;
    allowing the composition to solidify; and
    removing at least a portion of the solvent by vacuum sublimation.

2. The process according to claim 1, wherein the column is contacted with the composition at a first temperature, and the solvent is removed by vacuum sublimation at a second temperature.

3. The process according to claim 1, wherein the chromatographic medium is chosen from bead packings, film coatings, and expanded polymeric structures.

4. The process according to claim 1, wherein the solvent is chosen from maleic anhydride, dimethyl sulfone, cyclohexanol, p-dichlorobenzene, norcamphor, dimethyl formamide, 1-methyl-2-pyrrolidone, and succinonitrile.

5. The process according to claim 1, wherein the chromatography column is a gas chromatography column.

6. The process according to claim 1, wherein the column has a length ranging from 10 cm to 2 m, and a footprint ranging from 0.5 $cm^2$ to 2 $cm^2$.

7. The process according to claim 6, wherein the column is sealed with a cover layer by at least one of adhesion bonding, diffusion bonding, anodic bonding, welding, soldering, thermal fusion bonding, and deformation sealing.

8. The process according to claim 1, wherein at least some structures of the column are etched into a wafer.

9. The process according to claim 8, wherein said column is a gas chromatography column, and said wafer comprises a plurality of gas chromatography columns.

10. The process according to claim 1, wherein the column is sealed prior to removal of the solvent by vacuum sublimation.

11. The process according to claim 1, wherein the solvent is removed in a vacuum oven at a temperature below the melting point of the composition.

12. The process according to claim 1, wherein the column is contacted with the composition by at least one of spin-coating a composition onto a wafer comprising the column, suctioning the composition into the column, spray-coating the composition onto a wafer comprising the column, and submerging a wafer comprising the column into the composition.

13. A process for filling an elongated groove with a chromatographic medium, wherein the elongated groove comprises part of an unassembled miniaturized chromatographic column, said process comprising:
    exposing said elongated groove to a composition comprising a solvent and a chromatographic medium; and
    removing at least a portion of the solvent from the elongated groove by vacuum sublimation.

14. The process according to claim 13, wherein the groove is sealed prior to removing solvent from the groove by vacuum sublimation.

15. The process according to claim 14, wherein the groove is sealed by at least one of adhesion bonding, diffusion bonding, and anodic bonding of a cover layer.

16. The process according to claim 13, wherein the elongated groove is exposed to the composition by applying centrifugal forces to pack and retain the composition into the elongated groove.

17. The process according to claim 13, wherein the elongated groove contains an input aperture, and said groove is filled by inserting the composition through the input aperture.

18. The process according to claim 17, wherein the elongated groove contains an output aperture, and a vacuum is applied to the output aperture, such that the composition is suctioned from the input aperture.

19. The process according to claim 13, wherein the elongated groove is exposed to the composition at a first temperature, and the solvent is removed by vacuum sublimation at a second temperature.

20. A process for deposition of a stationary phase in a microfabricated gas chromatography column, comprising:
    combining the stationary phase with a solvent to form a composition, wherein the solvent is suitable for removal by vacuum distillation;
    filling at least a portion of the microfabricated gas chromatography column with the composition; and
    removing at least a portion of the solvent in the composition by vacuum sublimation.

* * * * *